United States Patent
Pessiot et al.

(10) Patent No.: US 11,795,482 B2
(45) Date of Patent: Oct. 24, 2023

(54) METHOD FOR PREPARING ORGANIC MOLECULES BY ANAEROBIC FERMENTATION

(71) Applicant: AFYREN, Clermont-Ferrand (FR)

(72) Inventors: Jeremy Jean-Paul Pessiot, La Charite sur Loire (FR); Michael Frederic Pierre Roussel, Clermont Ferrand (FR); Aurelien Antoine Bost, Clermont Ferrand (FR)

(73) Assignee: AFYREN, Clermont-Ferrand (FR)

( * ) Notice: Subject to any disclaimer, the term of this patent is extended or adjusted under 35 U.S.C. 154(b) by 108 days.

(21) Appl. No.: 17/286,669

(22) PCT Filed: Oct. 18, 2019

(86) PCT No.: PCT/EP2019/078329
§ 371 (c)(1),
(2) Date: Apr. 19, 2021

(87) PCT Pub. No.: WO2020/079210
PCT Pub. Date: Apr. 23, 2020

(65) Prior Publication Data
US 2022/0243231 A1    Aug. 4, 2022

(30) Foreign Application Priority Data
Oct. 19, 2018 (FR) ........................ 1859671

(51) Int. Cl.
*C12P 39/00* (2006.01)
*C12P 7/52* (2006.01)
*C12P 7/54* (2006.01)

(52) U.S. Cl.
CPC .................. *C12P 7/52* (2013.01); *C12P 7/54* (2013.01); *C12P 39/00* (2013.01)

(58) Field of Classification Search
CPC ................ C12P 7/52; C12P 7/54; C12P 39/00
See application file for complete search history.

(56) References Cited

FOREIGN PATENT DOCUMENTS

| EA | 32496 B1 | 6/2019 |
|----|----------|--------|
| EP | 1 892 300 A1 | 2/2008 |
| RU | 2649370 C2 | 4/2018 |
| WO | 2010/047815 A2 | 4/2010 |
| WO | 2014/100424 A1 | 6/2014 |
| WO | 2015/036683 A1 | 3/2015 |
| WO | 2016/012701 A1 | 1/2016 |
| WO | 2016/135396 A1 | 9/2016 |
| WO | 2016/135397 A1 | 9/2016 |
| WO | 2017/013335 A1 | 1/2017 |

OTHER PUBLICATIONS

Kitagawa K. et al., "Liquid for Promoting Odorless Fermentation and Decomposition of Organic Substance and Method for Manufacturing Compost From Organic Substance Under Odor Control Using It", JP 2004261714 A; English Machine translation; total pp. 1-20. (Year: 2004).*

Alkaya E., "Recovery of acids from anaerobic acidification broth by liquid-liquid extraction" (a Technical note), Chemosphere, vol. 77 (2009), pp. 1137-1142. (Year: 2009).*

Cheng et al., "1,3-Propanediol production by Klebsiella pneumoniae under different aeration strategies" Biotechnology Letters, vol. 26, 2004, pp. 911-915.

Botheju et al., "Oxygen Effects in Anaerobic Digestion—A Review", The Open Waste Management Journal, 2011, vol. 4, pp. 1-19.

Lim et al., "Microbial community structure reveals how microaeration improves fermentation during anaerobic co-digestion of brown water and food waste", Bioresource Technology, vol. 171, 2014, pp. 132-138.

Yilmaztekin et al., "Effects of Fermentation Temperature and Aeration on Production of Natural Isoamyl Acetate by *Williopsis saturnus* var. *saturnus*", Hindawi Publishing Corporation, BioMed Research International, vol. 2013, 2013, 6 pages.

Novikov, D.A., Isolation and purification of biotechnology products, Methodical manual, Minsk University, 2014.

* cited by examiner

*Primary Examiner* — Satyendra K Singh
(74) *Attorney, Agent, or Firm* — BCF LLP

(57) ABSTRACT

The present invention relates to the preparation of organic molecules by anaerobic fermentation of biomass, in which the fermentation liquor is aerated prior to the organic molecule recovery step.

14 Claims, No Drawings

METHOD FOR PREPARING ORGANIC MOLECULES BY ANAEROBIC FERMENTATION

CROSS-REFERENCE TO RELATED APPLICATIONS

This application is a national phase filing under 35 U.S.C. 371 of International Application No. PCT/EP2019/078329, filed on Oct. 18, 2019, which claims the benefit of French Patent Application No. 1859671, filed on Oct 19, 2018. The contents of the aforementioned applications are incorporated by reference in their entirety herein.

FIELD OF THE INVENTION

The present invention relates to the preparation of organic molecules by anaerobic fermentation of biomass, in which the fermentation liquor is aerated prior to the organic molecule recovery step.

STATE OF THE ART

Various processes are known for the preparation of organic molecules, in particular organic acids, by anaerobic fermentation of a biomass, in particular by fermentation of molasses and/or pulp, comprising in particular the steps of anaerobic fermentation of molasses and/or pulp in an aqueous fermentation medium, recovery of a fermentation liquor from the fermentation must and isolation of the organic molecules from the fermentation liquor. These processes and the conditions for carrying out the various steps are in particular described in the patent applications WO 2016/135396, WO 2016/135397, WO 2016/012701, WO 2017/013335, WO 2015/036683, WO 2014/100424 and WO 2010/047815.

The isolation of organic molecules from the fermentation liquor is generally preceded by a concentration of the fermentation liquor by evaporation of water. However, this evaporation step can lead to the loss of some of the organic molecules with the evaporation of the water and a loss in final yield.

It is therefore advantageous to find a robust and economical process that limits or even eliminates the loss of organic molecules during the evaporation of water to concentrate the fermentation liquor.

DISCLOSURE OF THE INVENTION

The invention resides in a simple step that consists in aerating the fermentation liquor before its concentration.

The invention thus relates to a process for preparing organic molecules comprising the steps of a) anaerobically fermenting a biomass in an aqueous fermentation medium, b) recovering a fermentation liquor from the fermentation must, and c) recovering organic molecules from the fermentation liquor, in which the fermentation liquor is aerated prior to the step c) of recovering the molecules.

Advantageously, the step c) of recovering the organic molecules comprises a step c1) of concentrating the fermentation liquor which precedes a step c2) of recovering the organic molecules from the concentrated fermentation liquor.

Advantageously and preferably, the object of the fermentation process is to produce organic acids, more particularly volatile organic acids, such as acetic, propionic, butyric, isobutyric, valeric, isovaleric, caproic acids and mixtures thereof.

DETAILED DESCRIPTION OF THE INVENTION

Processes for preparing organic molecules by anaerobic fermentation comprise the steps of a) anaerobically fermenting a biomass in an aqueous fermentation medium, b) recovering a fermentation liquor from the fermentation must, and recovering the organic molecules from the fermentation liquor, in which the fermentation liquor is aerated prior to the step c) of recovering the molecules.

The invention relates to an improvement of these anaerobic fermentation processes which consists in aerating the fermentation liquor before the recovery of these organic molecules.

The organic molecules produced in these anaerobic fermentation processes are in particular alcohols, organic acids, and in particular volatile organic acids, derivatives of these organic acids such as polyhydroxyalkanoates or esters, or amino acids.

Advantageously and preferably, the object of the fermentation process is to produce organic acids, more particularly volatile organic acids, such as acetic, propionic, butyric, isobutyric, valeric, isovaleric, caproic acids and mixtures thereof.

According to the invention, the biomass comprises any biomass that can be fermented in anaerobic mode, comprising the nutrients necessary for the growth of the anaerobic microorganisms and the production of the selected organic molecules. The different exploitable biomasses are well known to the person skilled in the art according to the anaerobic fermentation processes implemented. These fermentable biomasses are for example co-products from agriculture or the agri-foods industry such as cereal waste, potato sorting waste, slaughterhouse waste, brewery draff, vinasse or livestock effluents. All methanizable substrates are also examples of fermentable biomasses. The classic fermentation substrates used in biotechnology or in the agri-foods industry such as sucrose, glucose, fructose or alcohols such as glycerol are also examples of fermentable biomass.

According to a particular embodiment of the invention, the biomass is molasses and/or beet pulp.

According to a more preferred embodiment of the invention, the anaerobic fermentation process is carried out with molasses and/or pulp as carbon source, for the preparation of organic acids, in particular volatile organic acids as identified above.

The invention consists in aerating the fermentation liquor before the recovery of the organic molecules and the skilled person will know how to determine the most appropriate means and conditions of aeration of the fermentation liquor according to the volume of liquor to be treated and the organic molecules to be recovered.

In particular, aeration can be achieved by introducing air or bubbling air through the fermentation liquor, or by simply stirring the fermentation liquor in contact with air by any suitable means such as recirculation pumps, spargers, venturi mixers etc.

Preferentially, the aeration is obtained by stirring the fermentation liquor.

Without wanting to limit the invention or to be bound to any theory, it may be understood that the fermentation liquor from an anaerobic fermentation step includes high amounts of dissolved carbon dioxide. It is possible that aeration, by removing the dissolved carbon dioxide in the fermentation liquor, may increase the pH of the liquor.

It was indeed found that the aeration of the fermentation liquor raised its pH and that the more the pH of the liquor was acid, the more the organic molecules were entrained with the evaporation of water, for example in the event of recovery with evaporation of water, as in a concentration step.

Advantageously, aeration is maintained until a fermentation liquor with a pH of at least 7, preferably at least 8, is obtained.

Generally, aeration is maintained for at least 15 minutes, and can be up to 30 minutes or more. The aeration time will essentially depend on the pH of the fermentation liquor recovered at the end of the fermentation, the skilled person knowing how to determine the aeration time according to this pH, but also on the organic molecules to be recovered and the methods for recovering said organic molecules.

This pH increase is particularly suitable when the organic molecules are organic acids, more particularly volatile organic acids such as acetic, propionic, butyric, isobutyric, valeric, isovaleric, caproic acids and mixtures thereof.

The processes and conditions for carrying out the various steps are in particular described in the patent applications WO 2016/135396, WO 2016/135397, WO 2016/012701, WO 2017/013335, WO 2015/036683, WO 2014/100424 and WO 2010/047815.

The fermentation step a) will generally be implemented in mesophilic and anaerobic mode in a stirred fermenter. The culture mode can be continuous or discontinuous.

The biomass, in particular molasses or pulp, used for the fermentation is preferably residue from the sugar industry, in particular from sugar cane or sugar beet processing, preferably sugar beet pulp or sugar beet molasses.

Molasses and pulp can be used together in the same fermenter in any proportion, or separately in different fermenters.

Preferentially, pulp and/or molasses are the only carbon sources for anaerobic fermentation.

Anaerobic fermentation is generally carried out with microorganisms alone or in mixtures. It can be lines and mixtures of microorganisms seeded in the biomass for the beginning of fermentation. It can also be the autochthonous flora of the biomass which develops under the conditions of anaerobic culture.

The aqueous medium is water. According to a particular embodiment of the invention, the aqueous fermentation medium consists of water and vinasse mixed in any proportion. The aqueous fermentation medium can be supplemented with vitamins, yeast extract or any other adjuvant allowing an optimization of the fermentation performance.

For step b), the recovery is done at the end of fermentation according to usual filtration techniques to eliminate the potential solid residues present in the fermentation must, for example by centrifugation, centrifugal decantation, etc.

The aeration step is done on a liquid medium after fermentation where the state of the art describes the influence of aeration on the fermentation conditions, equivalent to step a) of the process according to the invention, upstream of step b) of recovering the fermentation liquor (Wei & al., 2014; EP 1 892 300; Cheng & al., 2004; Yimalztekin & al., 2013; Botheju & al., 2011).

The process for preparing organic molecules by anaerobic fermentation according to the invention can therefore also be described as comprising the following steps a) anaerobically fermenting a biomass in an aqueous fermentation medium, b) recovering a fermentation liquor from the fermentation must b2) aerating the fermentation liquor and c) recovering organic molecules from the aerated fermentation liquor.

The step c) of recovering the organic molecules is generally done by extraction, precipitation and/or distillation.

Advantageously, this step c) of recovering the organic molecules comprises a step c1) of concentrating the fermentation liquor which precedes a step c2) of recovering the organic molecules from the concentrated fermentation liquor.

The concentration step c1) is carried out according to the usual evaporation methods, known to the person skilled in the art.

The step c2) of recovering the organic molecules is advantageously carried out on the concentrated fermentation liquor after removal of at least part of the water and, if need be, with the addition of an organic solvent to promote the partitioning of the various molecules. Particular mention may be made of the extraction methods described in the applications WO 2015/036683, WO 2014/100424. The skilled person knows and will know how to choose the means best suited to the organic molecules to be isolated, this step not being limiting with respect to the invention, which first concerns the concentration step c1).

According to a particular embodiment, the step c2) of recovering the organic molecules is preceded by a step of acidification by addition of a strong acid, in particular sulfuric acid, down to a pH lower than 5, which can go down to 3 or less.

This addition of a strong acid is particularly appropriate before isolating organic acids, and more particularly volatile organic acids.

The fermentation liquor can come from a single fermentation must or from a mixture of several fermentation liquors from several fermentation musts, if need be after concentration. In this case, each fermentation must can come independently from the fermentation of pulp or molasses or from a mixture of pulp and molasses.

EXAMPLES

Anaerobic fermentation of organic by-products from sugar factories such as sugar beet molasses is carried out in industrial fermenters. The pH of the fermentation musts is regulated with potash. The results of the aeration experiments to raise the pH are presented in the tables below. At the end of fermentation, the fermentation liquor is recovered and aerated via a recirculation pump. The pH of the liquor is measured after a first aeration time of 1 or 2 minutes, then at the end of aeration.

Table 1 below summarizes the results of pH increase by aeration at different times from various liquors from anaerobic fermentation of molasses-type agro-industrial co-products.

TABLE 1

| Exp | Initial pH | Aeration time 1 | pH no. 1 | Aeration time 2 | Final pH |
|---|---|---|---|---|---|
| No. 1 | 6.76 | 1 min | 7.06 | 15 min | 8.38 |
| No. 2 | 6.53 | 2 min | 7.07 | 15 min | 8.31 |

TABLE 1-continued

| Exp | Initial pH | Aeration time 1 | pH no. 1 | Aeration time 2 | Final pH |
|---|---|---|---|---|---|
| No. 3 | 6.20 | 2 min | 6.45 | 30 min | 7.25 |
| No. 4 | 6.62 | 1 min | 7.00 | 15 min | 8.30 |

Following various anaerobic fermentations on agro-industrial co-products, the fermentation liquors are evaporated with or without a prior aeration step by stirring with a recirculation pump. The amounts of volatile fatty acids (VFA) in the evaporation condensate are measured. The results of the various experiments are shown in Table 2 below.

TABLE 2

| Exp | pH | [VFA] g/L condensates | Aeration before evasoration |
|---|---|---|---|
| No. 1 | 4.99 | 7.67 | NO |
| No. 2 | 5.85 | 3.09 | NO |
| No. 3 | 6.08 | 0.86 | NO |
| No. 4 | 6.10 | 0.76 | NO |
| No. 5 | 7.94 | 0.14 | YES |
| No. 6 | 7.87 | 0.27 | YES |
| No. 7 | 8.30 | 0.28 | YES |
| No. 8 | 8.46 | 0.32 | YES |

These results show that the aeration step limits the entrainment of volatile fatty acids with water during the concentration of the fermentation liquor and thus decreases the losses of these compounds likely to be recovered from the concentrated liquor.

REFERENCES

Botheju & al., 2011, The Open Waste Management Journal, vol. 4, no. 1, 1-19
Cheng & al., 2004, Biotechnology Letters, vol. 26, no. 11, 911-915
Wei & al., 2014, Bioresource Technology, vol. 171, 132-138
Yimalztekin & al., 2013, Biomed Research International, vol. 2013, 1-6
EP 1 892 300
WO 2010/047815, WO 2014/100424, WO2015/036683, WO 2016/012701, WO 2016/135397, WO 2016/135396, WO 2017/013335

The invention claimed is:

1. A process for recovering volatile organic molecules from an anaerobically fermented biomass, the process comprising the steps of:
    a) separating a fermentation liquor and a fermentation must from the fermented biomass,
    b) aerating the fermentation liquor obtained in step a) by introducing air through the fermentation liquor and/or by stirring in contact with air, and
    c) recovering organic molecules from the fermentation liquor of step b).

2. The process as claimed in claim 1, wherein the aeration is maintained until a fermentation liquor having a pH of at least 7 is obtained.

3. The process as claimed in claim 1, wherein the aeration is maintained until a fermentation liquor having a pH of at least 8 is obtained.

4. The process as claimed in claim 1, wherein the organic molecules are selected from the group consisting of organic acids and organic acid derivatives.

5. The process as claimed in claim 4, wherein the volatile organic acids are selected from the group consisting of acetic, propionic, butyric, isobutyric, valeric, isovaleric, caproic acids and mixtures thereof.

6. The process as claimed in claim 1, wherein the biomass is selected from the group consisting of molasses, pulp and mixtures thereof.

7. The process as claimed in claim 1, wherein step c) further comprises concentrating the fermentation liquor and recovering the organic molecules from the concentrated fermentation liquor.

8. A process for preparing volatile organic acids by biomass fermentation comprising:
    a) anaerobically fermenting a biomass in an aqueous fermentation medium,
    b) separating a fermentation liquor and a fermentation must from the fermented biomass of step a),
    c) aerating the fermentation liquor obtained in step b) by introducing air through the fermentation liquor and/or by stirring in contact with air,
    d) concentrating the aerated fermentation liquor of step c), and
    e) recovering volatile organic acids from the concentrated aerated fermentation liquor of step d).

9. The process as claimed in claim 8, wherein the volatile organic acids are selected from the group consisting of acetic, propionic, butyric, isobutyric, valeric, isovaleric, caproic acids and mixtures thereof.

10. The process as claimed in claim 8, further comprising acidifying the concentrated aerated fermentation liquor obtained in step d) by addition of a strong acid down to a pH of 5.0 or less, prior to recovering the volatile organic acids in step e).

11. The process as claimed in claim 10, wherein the strong acid is sulfuric acid.

12. The process as claimed in claim 10, wherein the concentrated aerated fermentation liquor is acidified down to a pH of 3.0 or less.

13. The process as claimed din claim 8, wherein the aeration is maintained until a fermentation liquor having a pH of at least 7.0 is obtained.

14. The process as claimed in claim 8, wherein the aeration is maintained until a fermentation liquor having a pH of at least 8.0 is obtained.

* * * * *